US005702401A

United States Patent [19]

Shaffer

[11] Patent Number: 5,702,401

[45] Date of Patent: Dec. 30, 1997

[54] INTRA-ARTICULAR MEASURING DEVICE

[76] Inventor: Benjamin Shaffer, 2111 Wisconsin Ave. NW., Apt. 305, Washington, D.C. 20007

[21] Appl. No.: 366,514

[22] Filed: Dec. 30, 1994

Related U.S. Application Data

[62] Division of Ser. No. 83,753, Jun. 28, 1993, abandoned.

[51] Int. Cl.$^6$ .......... A61B 17/56

[52] U.S. Cl. .......... 606/102

[58] Field of Search .......... 606/205, 86, 102; 128/774, 775, 777, 778, 780; 33/143, 512

[56] References Cited

U.S. PATENT DOCUMENTS

| | | | |
|---|---|---|---|
| 490,860 | 1/1893 | Snoeck . | |
| 4,033,043 | 7/1977 | Cunningham | 33/143 |
| 4,121,572 | 10/1978 | Krzeminski | 128/778 |
| 4,341,206 | 7/1982 | Perrett et al. . | |
| 4,450,834 | 5/1984 | Fischer . | |
| 4,726,121 | 2/1988 | Ray et al. | 33/143 |
| 4,779,349 | 10/1988 | Odensten et al. | 33/143 |
| 5,010,892 | 4/1991 | Colvin et al. | 128/774 |
| 5,013,318 | 5/1991 | Spranza, III | 606/102 |
| 5,122,146 | 6/1992 | Chapman et al. | 606/102 |
| 5,139,520 | 8/1992 | Rosenberg | 623/13 |
| 5,284,162 | 2/1994 | Wilk | 606/205 |
| 5,292,309 | 3/1994 | Van Tassel et al. | 604/117 |

FOREIGN PATENT DOCUMENTS 8800197.0 11/1988 Germany .

*Primary Examiner*—Guy V. Tucker

*Attorney, Agent, or Firm*—Fish & Richardson P.C.

[57] ABSTRACT

An intra-articular measuring device and method of using same, the device including a hollow handle defining a first passageway, and a hollow tube extending from the distal end of the hollow handle, the tube having a second passageway extending therethrough. The hollow tube carries a projection near its distal end for seating on a first selected region of a first bone, such as a tibial insertion point on a tibial plateau. The device further includes a probe slideably disposed within the first and second passageways, the hollow tube having a curvature sufficient to direct a distal end of the probe to a second selected region on a second bone, such as a femoral insertion point on a femur, to enable measurement of the distance between the first and second selected regions. Preferably, the probe includes a shaft extending proximally beyond the handle, the shaft carrying a gauge alignable with the proximal end of the handle to indicate the distance between the first and second selected regions.

4 Claims, 5 Drawing Sheets

120

132

110

INTRA-ARTICULAR MEASURING DEVICE

This is a divisional of application Ser. No. 08/083,753, filed Jun. 28, 1993, now abandoned.

This invention relates to a surgical instrument for measuring the actual length needed for a replacement ligament.

BACKGROUND OF THE INVENTION

There are a number of surgical procedures in which an implant such as an interference screw is placed into a bone of a patient. During reconstruction of an anterior cruciate ligament (ACL) using a patellar tendon graft, the graft is harvested having a bone plug at each end of the replacement ligament. One or both plugs are secured within a bone tunnel using an interference screw such as disclosed in U.S. Pat. Nos. 5,139,499 and 5,139,520, incorporated herein by reference.

In one technique of ACL reconstruction using a patellar tendon graft, a portal is made by incision in the soft tissue of the knee, a tunnel is formed in the bone by inserting a drill bit through the portal, a bone plug end of the replacement graft is inserted into the tunnel, and an interference screw is placed through the same portal into the tunnel to secure the bone plug. In some situations, it is difficult to manipulate the screw and driver together through the portal. If the screw becomes dislodged from the driver and drops into the joint, it is a time consuming process to retrieve the screw.

Therefore, it is an object of the present invention to provide an intra-articular measuring device which accurately measures the length of a replacemtn graft to be installed between two bones.

This invention features an intra-articular measuring device including a hollow handle defining a first passageway, and a hollow tube extending from the distal end of the hollow handle. The hollow tube has a second passageway extending therethrough and carries a projection near its distal end for seating on a first selected region of a first bone, such as a tibial insertion point on a tibial plateau. The device further includes a probe slideably disposed within the first and second passageways, the hollow tube having a curvature sufficient to direct a distal end of the probe to a second selected region on a second bone, such as a femoral insertion point on a femur, to enable measurement of the distance between the first and second selected regions. Preferably, the probe includes a shaft extending proximally beyond the handle, the shaft carrying a gauge alignable with the proximal end of the handle to indicate and se distance between the first and second selected regions.

This invention also features a method of measuring distance between first and second bones in a patient, the method including forming a portal in soft tissue of the patient to access the first and second bones, and providing an intra-articular measuring device as described above. The distal end of the tube is inserted through the portal, and the projection is placed on the first selected site. The probe is advanced distally until the second site is reached, and the distance between the first and second site is observed.

BRIEF DESCRIPTION OF THE DRAWINGS

Other objects, features and advantages will occur from the following description of preferred embodiments and the accompanying drawings, in which.

DETAILED DESCRIPTION OF THE DRAWINGS

This invention may be accomplished by an instrument having a holding member at its distal end which is pivotably movable relative to the instrument. The holding member has an element, such as threads or fingers, or a resilient lining, for holding an implant such as an interference screw. The instrument facilitates installation of the implant into the holding member, retention of the implant during insertion into a patient, and deployment of the implant into its final position within a patient.

Figure 1:
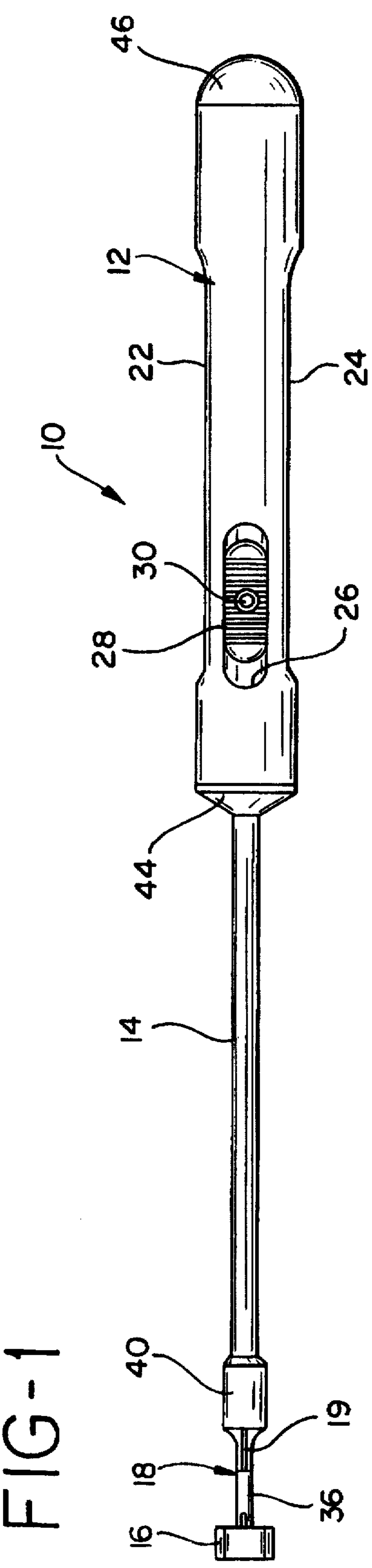
FIG. 1 is a top plan view of an adjustable implant holder instrument.
Figure 2:
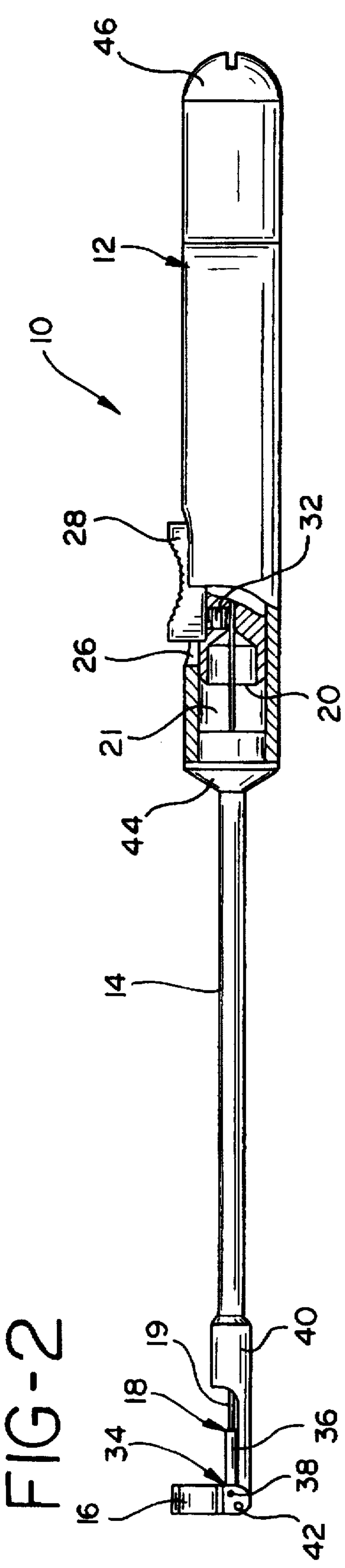
FIG. 2 is a side, partial cross-sectional view of the instrument of FIG. 1.

Adjustable screw holder instrument 10, FIGS. 1 and 2, has a proximal handle 12, a hollow shaft 14, a screw holding collar 16, and a connecting mechanism 18 including a rod 19 which is interconnected at its distal end with the collar 16 and at is proximal end with an actuating member 20. The actuating member 20 is a cylinder which reciprocates within a space 21 within handle 12. The handle 12 further defines recesses 22 and 24 to facilitate gripping of the handle 12 by the fingers of a hand, and defines an upper opening 26 through which a sliding actuating element 28 projects. The element 28 is attached by a cap screw 30 to the cylinder 20. The proximal end of the connecting rod 19 is engaged by a separate setscrew 32. The cylinder 20 preferably is coated with a substance having a low coefficient of friction such as Teflon or Silverstone polymer.

The proximal end of connecting mechanism 18 includes a pivot assembly 34 having a rectangular bar 36 with opposing distal tangs 38 which engage the screw holding collar 16. The wire 19 of connecting rod 18 is soldered to the rectangular piece 36. The screw holding collar 16 is connected to a support 40 by a pivot pin 42 such as a metal dowel. The support 40 is soldered or welded to the tube 14 which, in turn, is soldered to a conical adapter 44 that is welded to the handle 12. Proximal end cap 46 is threadably attached to the proximal end of the handle 12.

In one construction, the handle 12 is manufactured from a 4.20 inch length of 303 stainless steel rod having an outer diameter of 0.62 inch, as are the material and outer diameter of adapter 44 and end cap 46. The cylinder 20 is 303 stainless steel rod having an outer diameter of 0.415 inch and a length of 1.3 inch, the actuator element 28 is machined from an aluminum ⅜ inch by ⅜ inch bar having a length of 0.75 inch, the rod 19 has an outer diameter of 0.31 inch, a length of 6 inches, and is made of 17-4 stainless steel. The support tube 14 is 420B stainless steel tube having an outer diameter of 0.224 inch, an inner diameter of 0.67 inch, and a length of 4 inches. The support 40 is manufactured of 17-4 pre-hardened stainless steel having an outer diameter of 0.25 inch and a length of 1.31 inch, and rectangular bar 36 is made of 17-4 pre-hardened stainless steel having a width of 0.09 inch, a height of 0.06 inch, and a length of 0.56 inch. The screw holding collar 16 is formed of 17-4 pre-hardened stainless steel, has an outer diameter of 0.626 inch with an internal thread having the same pitch as an interference screw to be carried by the collar 16, and has a length of 0.84 inch.

One use of an adjustable implant holder instrument according to the present invention is described as follows. During ACL reconstruction, a first portal 50 is made in soft tissue 52, and a tunnel 54 is made in a tibia 56 of a patient such as described in U.S. Pat. No. 5,139,520. A tunnel 58 is then formed in a femur 60, and a bone block 62 of a patellar tendon graft 64 is inserted within the femoral tunnel 58. A bone block 66 rests within the tibial tunnel 54. An arthroscope, not shown, is used to observe procedures conducted within the capsular region of the knee joint 68.

A second, anteromedial portal 70 is formed in the soft tissue 52, and an adjustable holder instrument 74 is inserted through the second portal 70. An interference screw 76, which previously has been threadably inserted into a holding collar 78, is aligned with the femoral tunnel 58 by manipulating pull wire 80 which changes the orientation of the holder 78 relative to a support 82.

Figure 4:
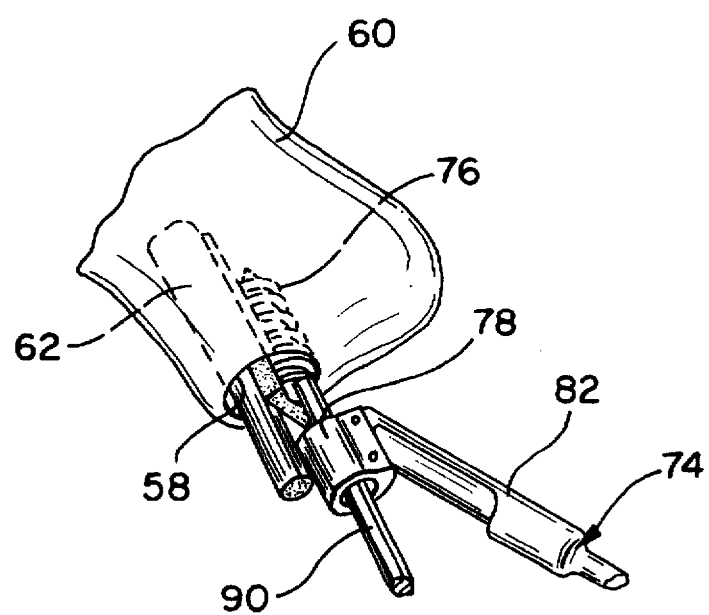
FIG. 4 is a schematic view of a portion of FIG. 3 after the driver has rotatably driven the screw out of the instrument and into the bone tunnel.
Figure 5:
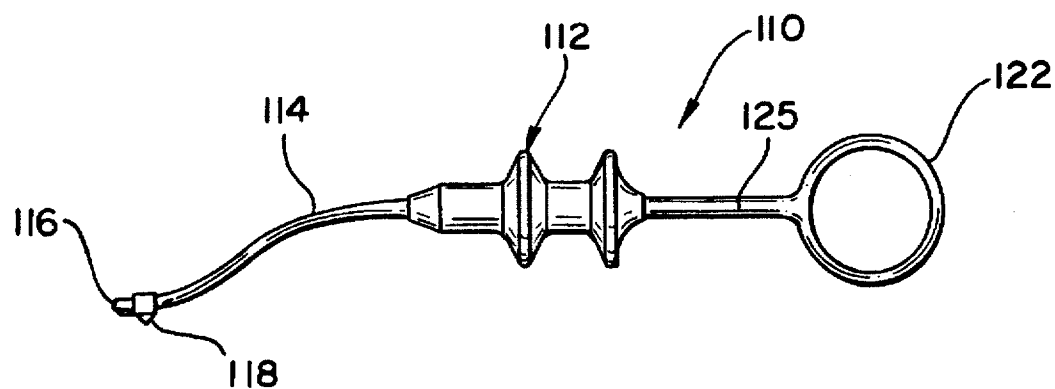
FIG. 5 is a schematic side view of a novel intra-articular measuring device according to the present invention.
Figure 6:
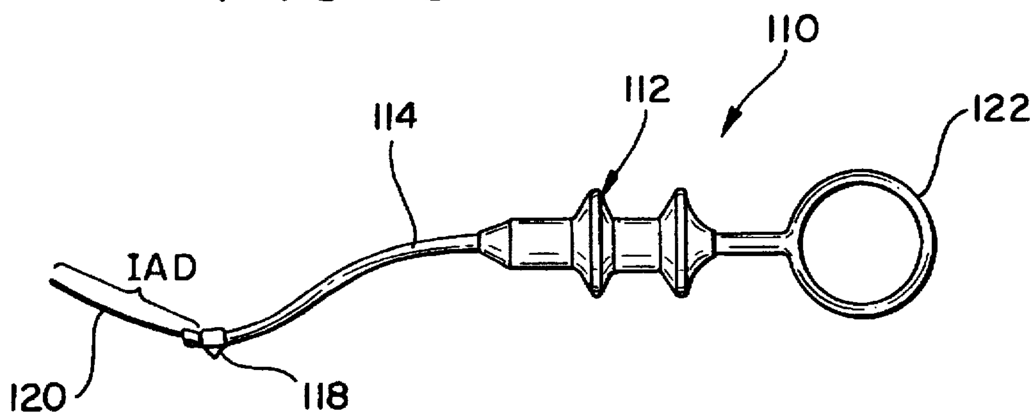
FIG. 6 shows the device of FIG. 5 with the measurement probe extended over an intra-articular distance IAD.
Figure 7:
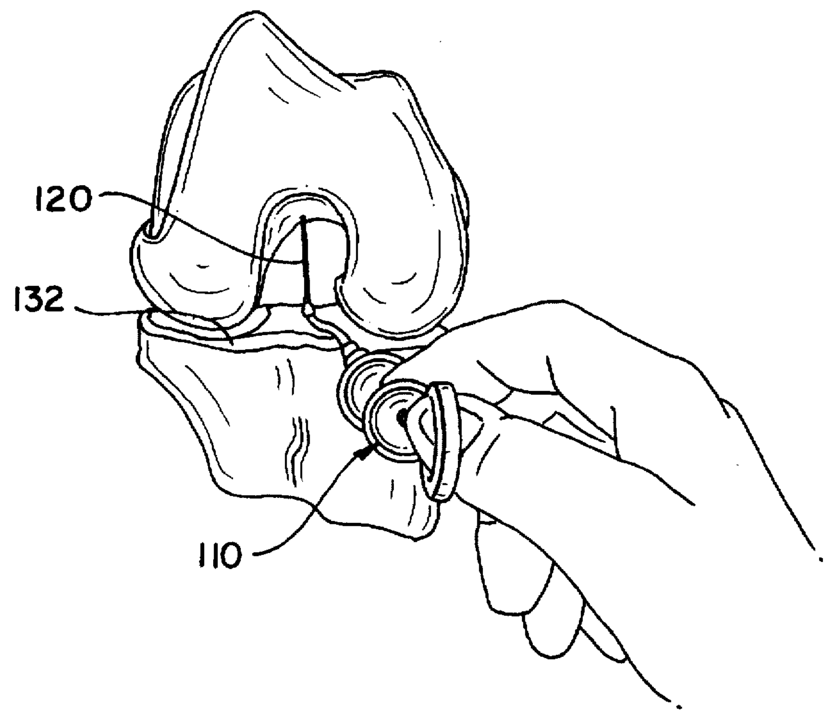
FIG. 7 is a schematic perspective view of the intra-articular device of FIGS. 5 and 6 being used within a knee joint.
Figure 8:
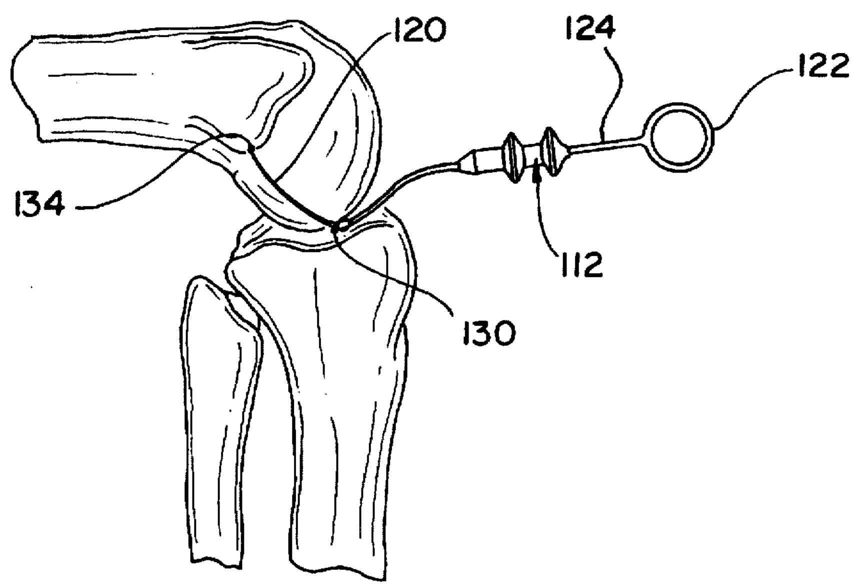
FIG. 8 is a schematic side view illustrating measurement of the distance IAD.
Figure 8A:
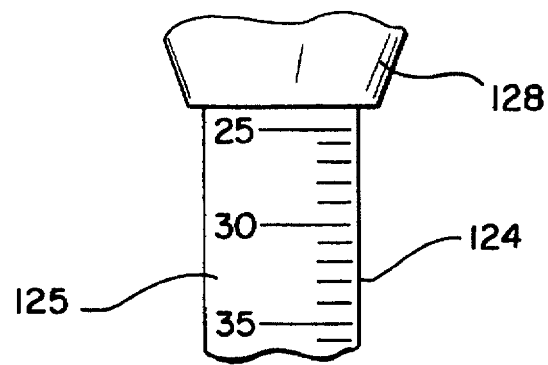
FIG. 8A is a view of the scale.

After proper orientation of the screw 76 is achieved as determined arthroscopically, a driver 90 is inserted through the first portal 50 and is engaged with the proximal end of the screw 76. The driver 90 is rotated to spirally drive the screw 76 into the femoral tunnel 58 as shown in FIG. 4.

Preferably, the actual length of the ligament to be replaced is measured using a novel intra-articular measuring device 110, FIGS. 5–8, having a handle 112 connected to a hollow tube 114 which terminates in a distal opening 116. A projection 118 is seated on the tibial plateau as described below. A probe 120 is advanceable beyond the opening 116 when finger loop 122 is advanced towards the handle 112. A gauge 124 on shaft 125 indicates the extension length of the probe 120, as shown in an enlarged view in FIG. 8.

In one construction, the handle 112 has a length of approximately 2.6 inch and the tube 114 projects approximately five inches distally beyond it. The probe 120 is 5.5 inch in length, and the finger loop 122 and the shaft 125 have a combined length of 3.1 inch. The gauge 124 carries markings at one mm increments between between 0 to 45 mm.

Figure 3:
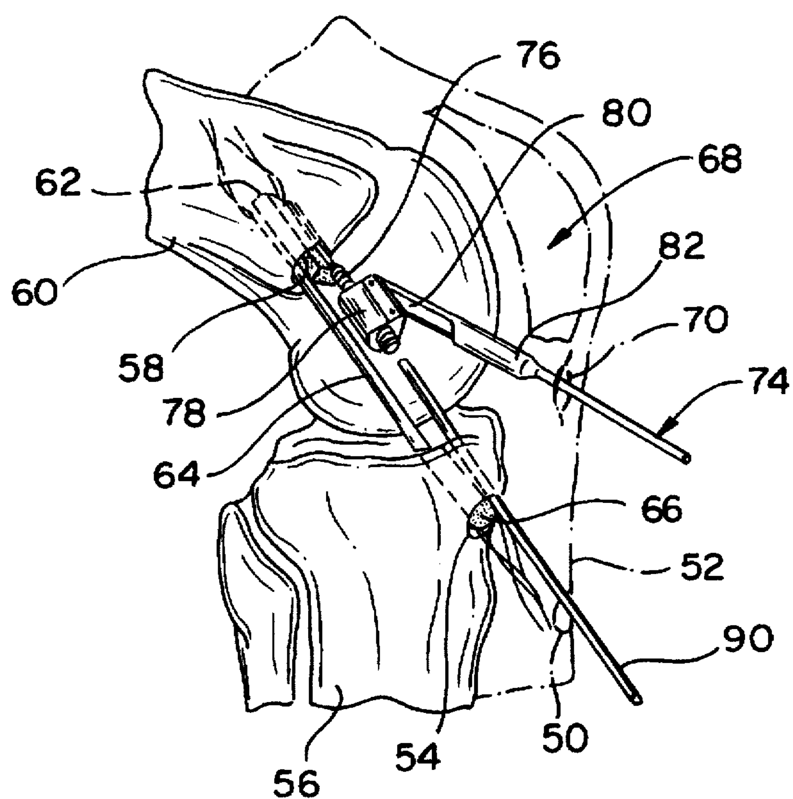
FIG. 3 is a schematic view of an instrument inserted into a knee of a patient together with a patellar tendon graft, an interference screw carried by the instrument, and a driver.

During use, the intra-articular measurement device 110 is inserted through the anteromedial portal 70, FIG. 3, until the projection 118 is seated at tibial insertion point 130 on the tibial plateau 132. The probe 120 is advanced thereafter until the femoral insertion point 134 is reached. To thereby read the exact intra-articular distance IAD between point 130 and point 134.

During a study of thirty-four bone-patellar tendon-bone autograph endoscopic ACL reconstructions, the intra-articular distance IAD was found to range from 21 mm to 33 mm, with the average being 26.3±3.0 mm. The novel intra-articular measuring device enables precise measurement of the distances to properly place a replacement ligament within the femoral and tibial tunnels.

Figure 9:
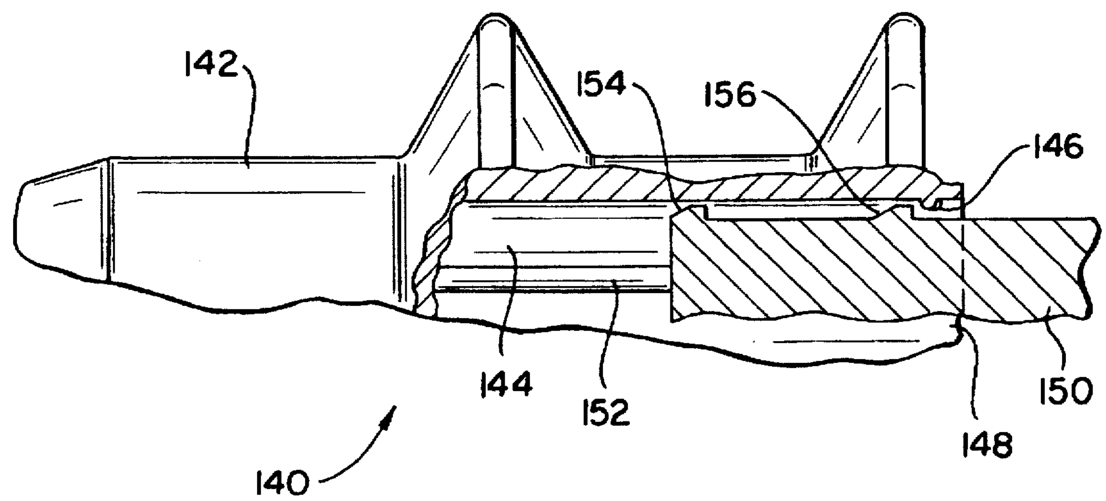
FIG. 9 is a partial cross-sectional top view of an alternative intra-articular device according to the present invention.

An improved intra-articular measuring device 140, FIG. 9, has a handle 142 which defines a passageway 144 and a proximal ridge 146 on either side of a proximal opening 148. A slideable shaft 150 is attached at its distal end to a probe 152 and defines ribs 154, 156 on either side. The ridge 146 and ribs 154,156 enhance stability during movement of the shaft 150 relative to the handle 142, serve to center shaft 150, and act as a stop members to inhibit inadvertent withdrawal of the shaft 150. In one construction, the ribs 154,156 have a height of 0.007 to 0.008 inch, a length of 0.030 inch, and a distal edge tapered at thirty degrees. Ridge 146 has a height of 0.006 inch.

Although specific features of the invention are shown in some drawings and not in others, this is for convenience only as each feature may be combined with any or all of the other features in accordance with the invention.

Other embodiments will occur to those skilled in the art and are within the following claims.

What is claimed is:

1. A method of measuring distance between a first bone and a second, different bone in a patient, said method comprising:
   - forming a portal in soft tissue of the patient to access the first bone and the second bone;
   - providing an intra-articular measuring device including:
     - a hollow handle having a distal end and a proximal end and defining a first passageway therebetween;
     - a hollow tube having a distal end, a proximal end, and a second passageway extending therebetween, said tube proximal end being connected to said handle distal end;
     - said hollow tube carrying a projection near said tube distal end for seating on a first selected region of the first bone;
     - a probe slidably disposed within said first and second passageways, and having a distal end and a proximal end, said hollow tube having a curvature sufficient to direct said distal end of said probe to a second selected region on the second, different bone to enable measurement of the distance between said first selected region and said second selected region when said distal probe end is advanced distally beyond said tube distal end to said second selected region;
   - inserting said tube distal end through the portal;
   - placing said projection on said first selected region;
   - advancing said probe distally beyond said tube distal end until said probe reaches said second selected region; and
   - observing the distance between said first and second regions based on an amount by which said probe has been advanced to reach said second selected region.

2. The method of claim 1 wherein said placing step includes placing said projection on a tibial insertion point on a tibial plateau as said first selected region, and said advancing step includes advancing said probe until said probe reaches a femoral insertion point on a femur as said second selected region.

3. The method of claim 1 wherein said probe further includes a shaft extending proximally beyond said handle proximal end, said shaft carrying a gauge alignable with said handle proximal end, said observing step including reading the distance between said first and second selected regions indicated on said gauge.

4. The method of claim 1 wherein said probe includes a finger loop attached to a proximal end of said shaft and said advancing step includes moving said probe distally with said finger loop until said second selected region is reached.

* * * * *